United States Patent [19]  
Akiyama

[11] 4,060,080  
[45] Nov. 29, 1977

[54] PLUG FOR LIVING BODY

[76] Inventor: Taichiro Akiyama, 2-19-23, Shimoochiai, Shinjuku-ku, Tokyo, Japan

[21] Appl. No.: 667,122

[22] Filed: Mar. 15, 1976

[30] Foreign Application Priority Data

Mar. 17, 1975 Japan .......................... 50-35609[U]  
Nov. 22, 1975 Japan .......................... 50-158874[U]

[51] Int. Cl.² ............................................. A61F 11/02  
[52] U.S. Cl. .................................................. 128/152  
[58] Field of Search ................. 128/152, 151, 140 N, 128/206, 341, 342, 344

[56] References Cited  
U.S. PATENT DOCUMENTS

| 734,498 | 7/1903 | Bachler | 128/341 |
|---|---|---|---|
| 2,499,045 | 2/1950 | Walker et al. | 128/344 |
| 2,541,520 | 2/1951 | Kegel | 128/344 |
| 2,691,985 | 10/1954 | Newsom | 128/342 |
| 2,850,012 | 9/1958 | Becker | 128/152 |
| 3,505,999 | 4/1970 | Harvey et al. | 128/152 |
| 3,799,170 | 3/1974 | Walsh et al. | 128/344 |

Primary Examiner—Robert W. Michell  
Assistant Examiner—Henry J. Reola  
Attorney, Agent, or Firm—McDougall, Hersh & Scott

[57] ABSTRACT

A plug for a living body includes a first chamber, a second chamber communicating with the first chamber, a holding means for holding the condition that the volume of the first chamber is reduced and a fluid put into the first and second chambers. The fluid is pressed into the second chamber when the volume of the first chamber is reduced so that the volume of the second chamber is increased. The external auditory miatus can be surely plugged with the plug.

8 Claims, 13 Drawing Figures

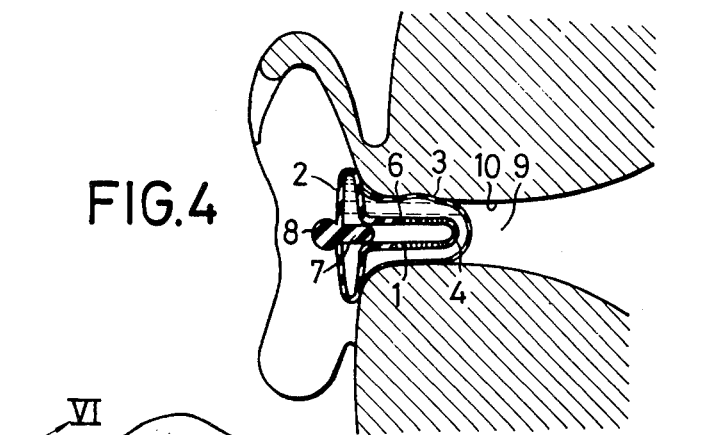
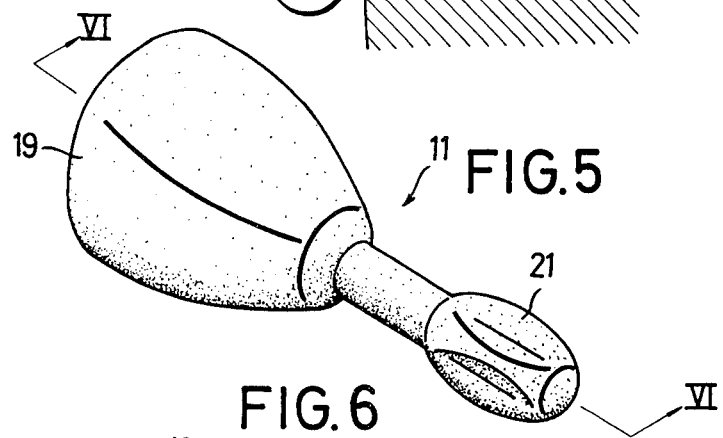
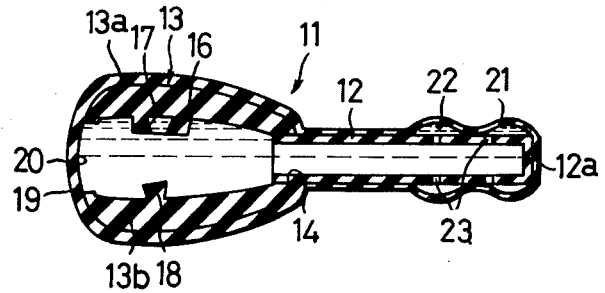
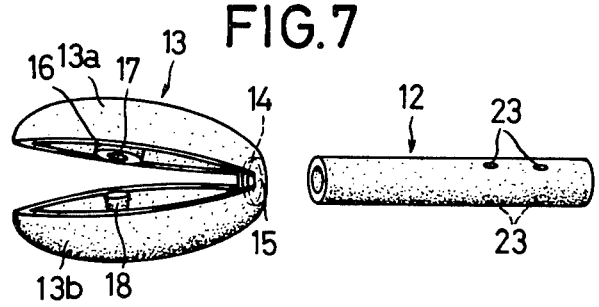

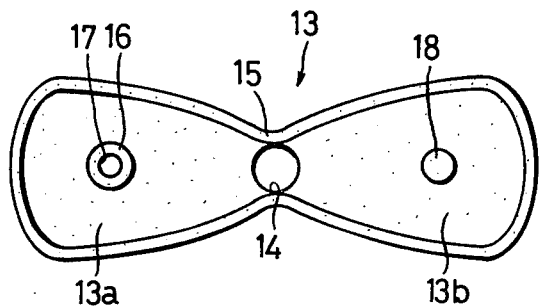
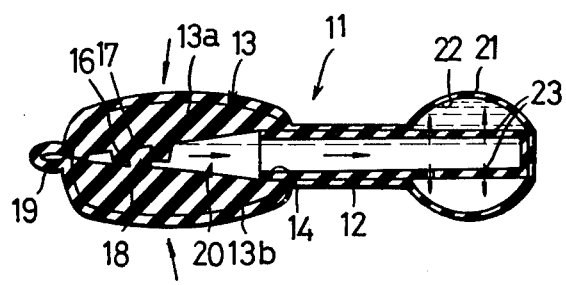
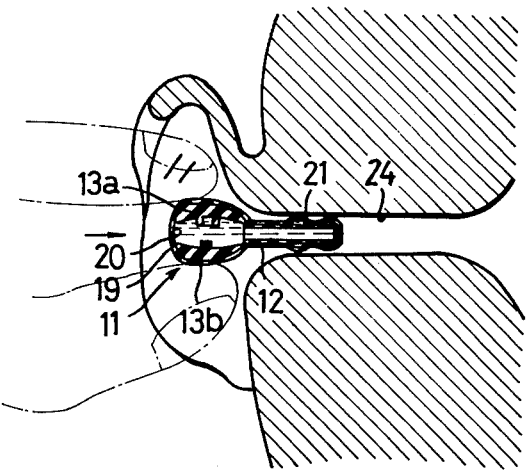

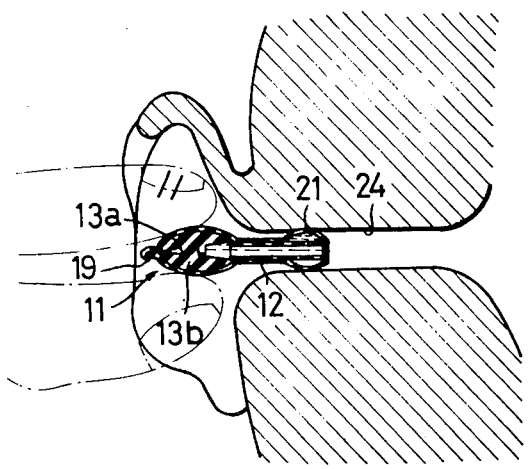
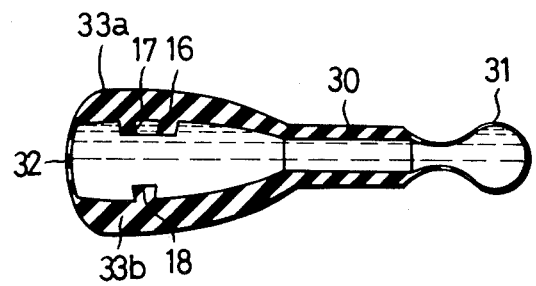
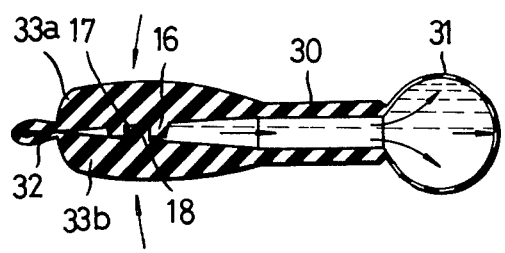

PLUG FOR LIVING BODY

BACKGROUND OF THE INVENTION

1. Field of the Invention

This invention relates to a plug for a living body, and more particularly to a plug with which the external auditory miatus or the nasal passage can be surely plugged.

2. Description of the Prior Art

It is often required to plug the organic passage of a living body or a human body for different purposes.

For example, the external auditory miatus needs to be plugged in order to shut off the sound. The nasal passage needs to be plugged in order to stop nosebleeding. A conventional ear plug is formed of rubber material such as silicone rubber into the shape to be insertable into the external auditory miatus. However, it is impossible to form the ear plug which can perfectly plug any of the external auditory miatus. Accordingly, the sound cannot perfectly be shut off from the eardrum. When the size of the ear plug is so large as to perfectly shut off the sound, it is difficult to insert the ear plug into the external auditory miatus. For the same reason, a conventional nose plug cannot perfectly plug the nasal passage. When the size of the nose plug is so large as to perfectly plug the nasal passage, it is difficult to insert the nose plug into the nasal passage.

SUMMARY OF THE INVENTION

Accordingly, it is an object of this invention to provide a plug for a living body which overcomes the disadvantages of the conventional plugs.

Another object of this invention is to provide a plug for a living body which can be easily inserted into the organic passage to perfectly plug the latter.

A further object of this invention is to provide a plug for a living body which can be easily taken out from the organic passage.

A still further object of this invention is to provide a plug for a living body which can be easily and surely handled.

In accordance with an aspect of this invention, a plug for a living body includes a first chamber; a second chamber communicating with the first chamber, a holding means for holding the condition that the volume of the first chamber is reduced, and a fluid put into the first and second chambers, the fluid being pressed into the second chamber when the volume of the first chamber is reduced so that the volume of the second chamber is correspondingly increased.

The above and other objects, features and advantages of this invention will become apparent from the following detailed description of illustrative embodiments shown in the accompanying drawings.

BRIEF DESCRIPTION OF THE DRAWINGS

FIG. 3 and FIG. 4 are cross-sectional views illustrating operation for plugging the external auditory miatus with the ear plug of FIG. 1;

FIG. 5 is a perspective view of an ear plug according to another embodiment of this invention;

FIG. 6 is a cross-sectional view taken along the line VI—VI of FIG. 5;

FIG. 7 is an exploded view of an important part of the ear plug of FIG. 5;

FIG. 8 is a developed view of a knob of the ear plug of FIG. 5;

FIG. 9 is a cross-sectional view of the ear plug when the knob is pinched by fingers;

FIG. 10 and FIG. 11 are cross-sectional views illustrating operation for plugging the external auditory miatus with the ear plug of FIG. 5;

FIG. 12 is a cross-sectional view of an ear plug according to a further embodiment of this invention; and FIG. 13 is a cross-sectional view of the ear plug of FIG. 12 when a pair of actuating members are pinched by fingers.

DESCRIPTION OF THE PREFERRED EMBODIMENTS

An ear plug according to one embodiment of this invention will be described with reference to FIG. 1 to FIG. 4.

Figure 1:
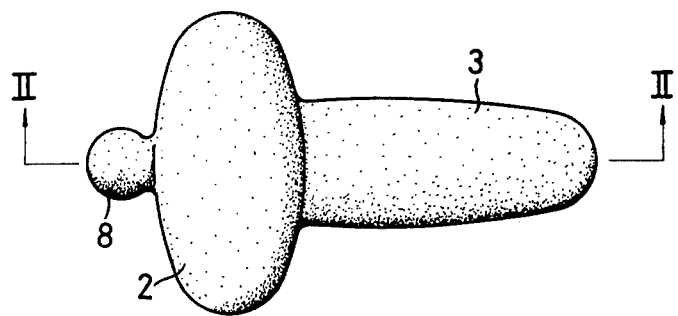
FIG. 1 is an elevational view of an ear plug according to one embodiment of this invention.
Figure 2:
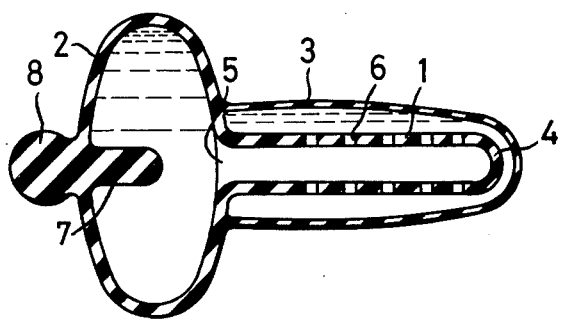
FIG. 2 is a cross-sectional view taken along the line II — II of FIG. 1.

Referring to FIG. 1 and FIG. 2, an ear plug includes a core tube 1, a hollow head 2 and an envelope 3 which are integrally formed. The core tube 1 is closed at its one end 4 and it is open at its another end 5. Numerous holes 6 are made in the wall of the core tube 1. It is formed of the same material as the hollow head 2, for example, of silicone rubber.

The hollow head 2 is combined with the open end 5 of the core tube 1. A projection 7 is formed on the inner wall of the hollow head 2 for plugging the open end 5 of the core tube 1. The diameter of the projection 7 is so large as to sufficiently plug the open end 5. A knob 8 is formed on the outer wall of the hollow head 2 in alignment with the projection 7.

The hollow head 2 is formed of flexible material such as silicone rubber. Accordingly, it can be easily deformed to insert the projection 7 into the core tube 1 through the open end 5, while the hollow head 2 is pushed with the knob 8 pinched by fingers. And when the projection 7 is drawn out from the core tube 1, the hollow head 2 can be easily restored to its original shape, as shown on FIG. 1 and FIG. 2. The projection 7 may be formed of any hard material, such as hard silicone rubber.

The envelope 3 is formed of soft thin material, such as a film of silicone rubber. It is combined with the hollow head 2 so as to envelope the core tube 1.

The core tube 1, the hollow head 2, the envelope 3, the projection 7 and the knob 8 may be integrally formed of the same material. A first chamber is formed by the core tube 1 and the hollow head 2, and a second chamber is formed by the envelope 3 and the core tube 1. The first chamber communicates with the second chamber through the numerous holes 6 of the core tube 1.

A liquid, such as glycerine, silicone oil, or fluorine-contained oil, or a gas such as air is put into the first and second chambers. While the envelope 3 is combined with the hollow head 2, the liquid or gas may be put into the first and second chambers. Or after the envelope 3 is combined with the hollow head 2, the liquid or gas may be put into the first and second chambers by a syringe. The content of the liquid or gas is so much that the envelope 3 may be so swelled or inflated with the liquid or gas as to effect a desirable operation when the liquid or gas is moved or pressed from the interior of the hollow head 2 and the core tube 1 or the first chamber into the interior of the envelope 3 or the second chamber, with the insertion of the projection 7 into the core tube 1.

Figure 3:
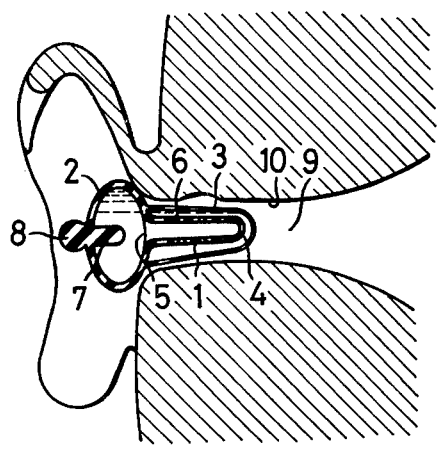

Next, operation of the above-described ear plug will be described with reference to FIG. 3 and FIG. 4. The withered envelope 3 is inserted into the external auditory miatus 9. The diameter of the withered envelope 3 is smaller than that of the external auditory miatus 9. The core tube 1 allows the withered envelope 3 to be easily inserted into the external auditory miatus 9. Next, the hollow head 2 is pushed with the knob 8 pinched by fingers, as shown on FIG. 4, to insert the projection 7 into the core tube 1. The liquid or gas contained by the hollow head 2 is flowed into the core tube 1 and then through the holes 6 into the envelope 3. As the result, the envelope 3 is swelled with the liquid or gas and it contacts closely with the inner surface 10 of the external auditory miatus 9. Thus, the external auditory miatus 9 is plugged up with the ear plug. Since the envelope 3 is formed of soft and thin material, it can contact closely with the inner surface 10 of the external auditory miatus 9. Even when the inner surface 10 is rough, the envelope 3 can follow well the shape of the inner surface 10. Thus, the external auditory miatus 9 can perfectly be plugged with the ear plug according to this invention. The sound can be surely shut off from the eardrum.

Moreover, since the liquid or gas is radially ejected into the envelope 3 from the holes 6 of the core tube 1 in operation, the envelope 3 is radially swelled, so that it can very smoothly contact with the inner surface 10 of the external auditory miatus.

Next, an ear plug according to an other embodiment of this invention will be described with reference to FIG. 5 to FIG. 11.

Referring to FIG. 6 and FIG. 7, an ear plug 11 includes a core tube 12 with the diameter of about 3 mm $\phi$, formed of silicone rubber. One end of the core tube 12 is inserted through a round hole 14 of a knob 13 and fixed to the round hole 14. The round hole 14 has the diameter of about 3 mm $\phi$. The knob 13 is formed of silicone rubber, having the thickness of 0.5 to 1 mm. FIG. 8 shows a developed view of the knob 13. The knob 13 comprises a pair of actuating members 13a and 13b which are connected to each other by a central connecting portion 15. The pair of actuating members 13a and 13b are elastic, so that they can be restored to their original positions as shown on FIG. 7 when operated. A ring 16 having a truncated-cone shaped recess 17 is formed on the one actuating member 13a, while a truncated-core shaped projection 18 is formed on the other actuating member 13b. The ring 16 can be fitted to the truncated-core shaped projection 18.

An envelope 19 formed of silicone rubber, relatively thick, for example, 0.4 to 0.5 mm thick, is attached to the knob 13 so as to envelope the latter. A first chamber 20 is formed by the envelope 19, the pair of actuating members 13a and 13b and the core tube 12. Another envelope 21 formed of silicone rubber, relatively thin, for example, 0.2 to 0.3 mm thick, contiguous to the one envelope 19, is attached to the core tube 12 so as to envelope the latter. The envelope 21 is adhered to one end 12a of the core tube 12 and to the cylindrical surface of the left half of the core tube 12. A second chamber 22 is formed by the core tube 12 and the envelope 21. Before operation, the envelope 21 is withered at the second chamber 22. Since the envelope 21 is formed of relatively thin material, it is inflatable and deflatable in operation. Plural small holes 23 are made in the wall of the core tube 12. The first chamber 20 and the second chamber 22 communicate with each other through the holes 23. A liquid such as water or ethlene glycol is put into the first and second chambers 20 and 22. The envelope 21 is designed to swell with the increase of the content of the liquid in the second chamber 22.

Next, operation of the above described ear plug 11 will be described.

When the knob 13 is pinched by fingers, the projection 18 of the one actuating member 13b is fitted into the recess 17 of the ring 16 of the other actuating member 13a, as shown on FIG. 9. The actuating members 13a and 13b are united with each other. On pinching, the liquid flows in the direction by the arrows on FIG. 9, since the volume of the first chamber 20 is reduced. The liquid is pressed into the second chamber 22 through the holes 23 of the core tube 12. As the result, the envelope 21 swells into nearly spherical shape. The shape is maintained, since the actuating members 13a and 13b are held by each other.

When the actuating members 13a and 13b are released from each other, the knob 13 is pinched laterally, namely in the direction perpendicular to the drawing, by fingers. The projection 18 and the ring 16 are slightly deformed, and so the actuating members 13a and 13b are restored to their original positions as shown on FIG. 6, due to the elasticity of the actuating members 13a and 13b.

Next, a method for plugging the external auditory miatus with the ear plug 11 will be described with reference to FIG. 10 and FIG. 11.

The envelope 21 of the ear plug 11 is inserted into the external auditory miatus 24, while the knob 13 is softly held by fingers. The core tube 12 allows the envelope 21 to be easily inserted into the external auditory miatus 24. Since the ear plug 11 can be well controlled and easily inserted, the ear does not ache. On inserting, the actuating members 13a and 13b are not united with each other. The insertion operation and the plugging operation as described hereafter can be separately effected.

After the insertion, the knob 13 is pinched by fingers, as shown on FIG. 11. The actuating members 13a and 13b are united with each other. The envelope 21 swells to contact closely with the surface of the external auditory miatus 24. Since the envelope 21 is soft and thin, it can easily follow the shape of the external auditory miatus 24. Thus, the external auditory miatus 24 can be surely plugged with the ear plug 11 and the sound can be surely shut off from the interior of the ear by the ear plug 11.

When the size of the external auditory miatus 24 is relatively small, the one envelope 19 swells relatively much at the front end of the ear plug 11. Accordingly, the ear plug 11 can be effective for different sizes of the external auditory miatus.

Next, an ear plug according to a further embodiment of this invention will be described with reference to FIG. 12 and FIG. 13. Parts in this embodiment which correspond to the parts in FIG. 5 to FIG. 11 are denoted by the same reference numerals, which will not be described in detail.

In this embodiment, parts corresponding to the envelopes 19 and 21 of the other embodiment are removed. A pair of actuating members 33a and 33b and a connecting tube 30 are integrally formed of the same material. The actuating members 33a and 33b are combined with each other through a thin connecting portion 32 formed of the same material as the actuating members 33a and 33b. A thin envelope portion 31 is formed on one end of the connecting tube 30. The thicknesses of the actuating members 33a and 33b, the connecting tube 30 and the envelope portion 31 may be nearly the same as those of the actuating members 13a and 13b, the core tube 12 and the envelope 21, of the embodiment of FIG. 5 to FIG. 11.

In operation of the ear plug of FIG. 12, the actuating members 33a and 33b are pinched by finger, in the direction as shown by the arrows on FIG. 13. With the pinch, the liquid is pressed into the envelope 31 through the connecting tube 30, as shown by the arrows on FIG. 13. As the result, the envelope 31 is inflated with the liquid, as shown on FIG. 13. Accordingly, this embodiment has the same effect as the embodiments of FIG. 1 to FIG. 11.

While preferred embodiments of the invention have been described using specific terms, such description is for illustrative purposes only, and it is to be understood that changes and variations may be made without departing from the spirit or scope of the following claims.

For example, although the ring 16 and the projection 18 are formed on the actuating members 13a and 13b so as to hold them by each other in the second and third embodiment, various holding means are possible. This invention may be applied to the plug of the gullet. In such a case, the plug according to this invention is combined with a cannula for feeding anethetic into the lung. The anethetic is prevented from flowing into the other organ, by the plug according to this invention.

What is claimed is:

1. A plug for insertion into a natural orifice of the body comprising
   a. a first chamber and an actuating means located therein;
   b. a tube member;
   c. a second chamber communicating with said first chamber through said tube member, said second chamber being formed by said tube member and a flexible envelope attached to the outer surface of said tube member, said first chamber being formed of a flexible envelope;
   d. said actuating means comprising a pair of substantially flat actuating members;
   e. said actuating means being formed of elastic material whereby facing wall surfaces thereof are normally held in spaced-apart relationship,
   f. cooperating locking means disposed on the respective facing wall surfaces whereby forcing said actuating means together operates to unite the actuating members and to hold the actuating members in the united position;
   g. and a fluid located in said first and second chambers, said fluid being pressed into said second chamber through said tube member when the volume of said first chamber is reduced by forcing said actuating members together so that the volume of said second chamber is increased.

2. A plug for insertion into a natural orifice of the body according to claim 1 wherein said locking means comprise a truncated-cone shaped recess positioned on one wall surface and a truncated-cone projection positioned on the opposite wall surface, said projection being receivable within said recess to achieve the locking function.

3. A plug for insertion into a natural orifice of the body according to claim 2 in which said recess is formed by a ring-shaped wall therearound.

4. A plug for insertion into a natural orifice of the body according to claim 1 wherein said flexible envelope of said second chamber extends beyond said second chamber and around said actuating means to form said first chamber.

5. A plug for insertion into a natural orifice of the body according to claim 4 wherein said actuating means includes means defined at one end thereof for attachment of the actuating means to one end of said tube, the members of said actuating means being pivotable about said connection with said tube.

6. A plug for insertion into a natural orifice of the body according to claim 1 in which said tube member functions as a core when the plug is inserted into the orifice, and said first chamber communicates with said second chamber through holes defined by said tube member.

7. A plug for insertion into a natural orifice of the body according to claim 1 in which said plug is an ear plug.

8. A plug for insertion into a natural orifice of the body according to claim 1 in which said plug is a nasal plug.

* * * * *